United States Patent [19]

Jaxa-Chamiec et al.

[11] Patent Number: 5,112,922
[45] Date of Patent: May 12, 1992

[54] POLYSTYRENE ANION EXCHANGE POLYMERS

[75] Inventors: Albert A. Jaxa-Chamiec, Rickmansworth; Deirdre M. B. Hickey, Welwyn, both of England

[73] Assignee: Smith Kline & French Laboratories, Welwyn Garden City, United Kingdom

[21] Appl. No.: 536,838

[22] Filed: Jun. 12, 1990

[30] Foreign Application Priority Data

Jun. 14, 1989 [GB] United Kingdom ............ 8913700.4

[51] Int. Cl.$^5$ ............................................. C08F 8/32
[52] U.S. Cl. .................................. 525/332.2; 521/32; 555/379; 555/380; 555/381; 555/382
[58] Field of Search ..................... 525/332.2; 521/32

[56] References Cited

U.S. PATENT DOCUMENTS

| | | |
|---|---|---|
| 3,989,088 | 8/1975 | Cohen et al. . |
| 4,101,460 | 7/1978 | Small et al. ............................ 521/28 |
| 4,198,395 | 4/1980 | De Simone . |
| 4,311,799 | 1/1982 | Miyake et al. . |
| 4,510,128 | 4/1985 | Khanna . |
| 4,532,128 | 7/1985 | Sheldon et al. . |
| 4,721,666 | 1/1988 | Yamanouchi et al. . |

FOREIGN PATENT DOCUMENTS

| | | |
|---|---|---|
| 929391 | 6/1963 | United Kingdom . |
| 1286949 | 12/1969 | United Kingdom . |
| 2026501-A | 2/1980 | United Kingdom . |

OTHER PUBLICATIONS

Walfish, et al., Water, Air & Soil Pollution 12:477-484.
Carpov, et al., J. Macromol. Sci. Chem., A22(5-7):9-07-929 (1985).
Takeuchi, et al., Chem. Pharm. Bull. 32(3):823-831 (1984).
Petrariu, et al., Revue Roumaine de Chimie, 25:145-154 (1980).
Wessling, et al., Makromol. Chem., suppl. 10/11:319-333 (1985).

Primary Examiner—Bernard Lipman
Attorney, Agent, or Firm—Wayne J. Dustman; Stuart R. Suter; Edward T. Lentz

[57] ABSTRACT

Polymers bearing a quaternary ammonium group are disclosed as being useful in lowering serum cholesterol levels in man. A compound of the invention is N,N-dimethyl-N-(2-(N,N-dimethylcarbamoyl)ethyl)-ammoniomethyl-substituted polystyrene, chloride salt.

16 Claims, No Drawings

POLYSTYRENE ANION EXCHANGE POLYMERS

The present invention relates to novel polymers, pharmaceutical compositions containing them and their use in the lowering of plasma cholesterol levels in humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange resins, in particular polystyrene resins can be used as sequestering agents to bind non-absorbed bile acids and salts in the intestinal tract, forming complexes which are then excreted in the faeces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering resins have been recognised as useful for the treatment of hypercholesterolaemia. In addition, it is now proven that reducing serum cholesterol with bile acid sequestrants has a beneficial effect on protecting against the occurrence of atherosclerosis.

One particular agent which is currently used to lower serum cholesterol levels in humans by binding bile acids in the intestinal tract is cholestyramine. Cholestyramine is a cross-linked anion exchange polystyrene resin bearing an ionisable trimethylammonium group bound to the polymer backbone. However, the use of this agent is associated with a number of undesirable side-effects, for example, it is unpalatable and must be taken in high doses and causes, in some cases, flatulence and other gut side-effects. In addition, its ability to bind bile acids lacks specificity and is inefficient with respect to the amounts of resin which it is necessary to use.

It is the object of the present invention to provide compounds which overcome the disadvantages of this known sequestering agent and provide improved bile acid sequestering agents which are useful for lowering serum cholesterol levels in humans.

The present invention therefore provides in a first aspect, polymers of structure (I):

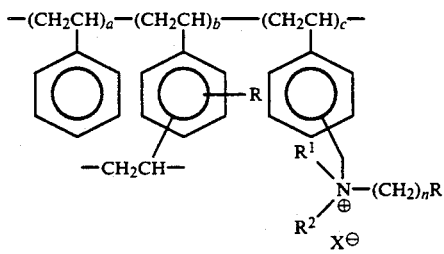

in which,
R is hydrogen or $R^1R^2{}^{\oplus}N(CH_2)_nR^3$;
$R^1$ and $R^2$ are each $C_{1-4}$alkyl;
$R^3$ is $CONR^4R^5$, $NR^4COR^6$, a phthalamido group, $COR^7$ or OH;

$R^4$ and $R^5$ are the same or different and are each hydrogen or $C_{1-8}$alkyl;
$R^6$ is $C_{1-4}$alkyl, $C_{1-4}$alkyl$C_{3-6}$cycloalkyl, $CF_3$ or $NR^4R^5$;
$R^7$ is hydroxy, $C_{1-4}$alkyl or $C_{1-4}$alkoxy;
n is 2 to 12;
a, b and c are numbers which indicate the relative molar percentages of the units present in said polymer, (b) being from 1 to 10 molar percent, and (c) being from 30 to 98 molar percent;
$X^{\ominus}$ is a counter ion.

Suitably the groups $R^1$ and $R^2$ are the same or different; preferably they are the same; most preferably $R^2$ and $R^3$ are both methyl.

Suitably $R^3$ is $CONR^4R^5$, $NR^4COR^6$, $COR^7$ or OH; preferably $R^3$ is $CONR^4R^5$.

Suitably $R^4$ and $R^5$ are the same or different and are each hydrogen or $C_{1-8}$alkyl; more suitably $R^4$ and $R^5$ are the same. Preferably $R^4$ and $R^5$ are both $C_{1-8}$alkyl, in particular $C_{1-4}$alkyl, especially methyl. Most preferably $R^4$ and $R^5$ are both hydrogen.

Suitably, $R^6$ is $C_{1-4}$alkyl, $CF_3$ or $NR^4R^5$; preferably $R^6$ is $NR^4R^5$ in which both $R^4$ and $R^5$ are hydrogen.

Suitably $R^7$ is hydroxy, $C_{1-4}$alkyl or $C_{1-4}$alkoxy; preferably $R^6$ is $C_{1-4}$alkoxy.

Suitably n is 2 to 12; preferably 2 to 7.

Suitably (b) is from 1 to 10 molar percent of said polymer, preferably (b) is from 2 to 8 molar percent of said polymer.

Suitably $X^{\ominus}$ is a counter ion as hereinafter defined; more suitably $X^{\ominus}$ is a chloride, sulphate or phosphate ion, preferably $X^{\ominus}$ is a chloride ion.

Other examples of suitable counter ions $X^{\ominus}$ will be apparent to those skilled in the art and include, in particular, physiologically acceptable counter ions such as halides, in particular chloride, phosphates or sulphates, bicarbonates, carbonates, formates, acetates, sulphonates, propionates, malonates, succinates, malates, tartrates, citrates, maleates, fumarates, ascorbates, glucuronates or the anions of amino acids such as aspartic or glutamic acid.

The polymers of the present invention are also characterised by their total exchange capacity i.e. the theoretical maximum capacity of the resin if each counter ion were to be exchanged with bile acid. In this specification the total exchange capacity is defined in terms of the number of milliequivalents of counter ion per gram of dry weight of polymer.

Suitable total exchange capacities are in the range of, for example where the counter ion $X^{\ominus}$ is chlorine, from 1.5 to 3.5 meq $Cl^-$ per gram of resin. Preferred within this range are resins having a total exchange capacity of between 2 and 3 meq $Cl^-$/gram of resin.

It is to be noted that the term ,bile acid, when used herein shall be taken to include bile acids, bile salts and conjugates thereof.

The polymers of the present invention can be prepared by processes analogous to those known in the art. For example by:

(a) reaction of a polymer of structure (II)

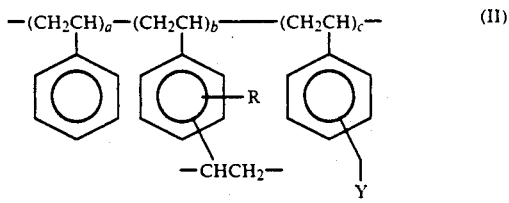

(II)

in which R, a, b and c are as described for structure (I) and Y is a group displaceable by an amine, with an amine of structure $R^1R^2N(CH_2)_nR^3$ (III) in which $R^1$ to $R^3$ and n are as described for structure (I); or (b) reaction of a polymer of structure (IV)

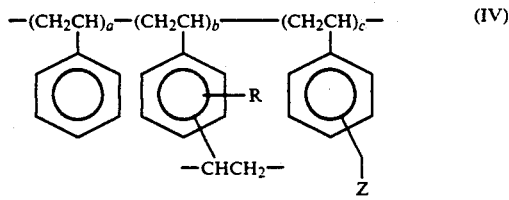

(IV)

in which R, a, b and c are as described for structure (I) and Z is $NR^1R^2$ or $NR^1(CH_2)_nR^3$ in which $R^1$ to $R^3$ and n are as described for structure (I), with a compound of structure $R^4Y$ (V) in which $R^4$ is $(CH_2)_nR^3$ when Z is $NR^1R^2$ or a group $R^2$ when Z is $NR^1(CH_2)_nR^3$, and Y is a group displaceable by an amine.

The reaction between a polymer of structure (II) and a compound of structure (III) can be carried out in a suitable solvent at elevated temperature. Suitable solvents included for example, a $C_{1-4}$alkanol, dimethylformamide or N-methylpyrrolidone. Preferably the reaction is carried out in dimethylformamide at a temperature of between about 60° and 80° for a period of between 24 hours or until the reaction is complete.

The reaction between a polymer of structure (IV) and a compound of structure (V) can be carried out in a suitable inert solvent such as a $C_{1-4}$ alkanol, dimethylformamide or N-methylpyrrolidone at elevated temperature.

The intermediate polymers of structure (II) are available commercially or can be prepared from readily available materials by methods known to those skilled in the art. For example polymers of structure (II) in which Y is chlorine can be prepared by reaction of chloromethylstyrene, styrene and divinyl benzene in an aqueous suspension comprising polyvinyl alcohol in the presence of an initiator at elevated temperature. Suitable initiators will be apparent to those skilled in the art and include, in particular azobisisobutyronitrile.

The intermediate polymers of structure (IV) can be prepared from the polymers of structure (II) by reaction with an amine of structure $HNR^1R^2$ or $HNR^1(CH_2)_nR^3$ in which $R^1$ to $R^3$ and n are as described for structure I under the same or similar conditions as indicated for the reaction of a compound of structure (II) and a compound of structure (III). Alternatively, the intermediate polymers of structure (IV) can be prepared by polymerisation of appropriate monomer mixtures under standard polymerisation conditions.

The intermediate polymers of structure (II) can be prepared directly from polystyrene by methods analogous to those known in the art, for example where $X^{\ominus}$ is chloride by chloromethylation of polystyrene.

The polystyrene resins of structure (I) have been found to bind bile acids both in in vitro and in in vivo models in that they increase the amount of bile acids in the faeces. As indicated earlier it is well recognised that removal of bile acids from the intestinal tract in this way lowers serum cholesterol levels and also has a beneficial effect on protecting against atherosclerosis and its dependent clinical conditions. The present invention therefore provides in a further aspect, the use of polystyrene resins of structure (I) in therapy, in particular for the lowering of serum cholesterol levels in mammals, including humans. In addition the polymers of structure (I) are expected to be of use in protecting against atherosclerosis and its sequelae.

In view of the foregoing the present invention also provides a method of lowering serum cholesterol levels in mammals which comprises administering to a mammal in need thereof an effective serum cholesterol lowering amount of a compound of structure (I); and a method of protecting against atherosclerosis.

When used in therapy in the methods of the invention, the polystyrene resins of structure (I) are in general administered in a pharmaceutical composition.

In a still further aspect of the present invention there is therefore provided a pharmaceutical composition comprising a polystyrene resin of structure (I) in association with a pharmaceutically acceptable carrier.

The compositions of the present invention can be prepared by techniques well known to those skilled in the art of pharmacy and include all those known for the formulation of polystyrene resins for human use.

The polymers are preferably administered as formulations in admixture with one or more conventional pharmaceutical excipients which are physically and chemically compatible with the polymer, which are nontoxic, are without deleterious side-effects but which confer appropriate properties on the dosage form.

In general, for liquid formulations aqueous pharmaceutically acceptable carriers such as water or aqueous dilute ethanol, propylene glycol, polyethylene glycol or glycerol or sorbitol solutions are preferred. Such formulations can also include flavouring and sweetening agents such as sucrose, fructose, inert sugar, cocoa, citric acid, ascorbic acid, fruit juices etc. In general, digestible oil or fat based carriers should be avoided or minimised as they contribute to the condition sought to be alleviated by use of the polymers. They are also subject to absorption by the polymers during prolonged contact, thus reducing the capacity of the polymer to absorb dietary fats after administration.

The polymers can also be prepared as concentrates, for dilution prior to administration, and as formulations suitable for direct oral administration. They can be administered orally ad libitum, on a relatively continuous basis for example by dispersing the polymer in drinks or food.

Preferably, the polymers are administered in tablet form or in gelatin capsules containing solid particulate polymer or an aqueous or semi-aqueous suspension of solid polymer containing a suitable suspending agent.

Preferably the polymer is administered in unit dosage form, each dosage unit containing preferably from 0.5 g to 1 g of polymer.

The daily dosage regimen for an adult patient may be, for example, an oral dose of between 1 and 10 g, preferably 1-5 g the compound being administered 1 to 4 times a day. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following examples indicate the properties and preparation of the polymers of the present invention. Temperatures are recorded in degrees centigrade. The exchange capacity of the ammonium substituted resins was determined by elemental analysis and/or potentiometric titration of chloride ion. Figures quoted are expressed as milli equivalents of exchangeable chloride ion per gram of dry resin weight.

EXAMPLE 1

(a) 3-Bromopropionyl chloride (25.7 g) was dissolved in dichloromethane (100 ml), cooled to 0° and a 25% aqueous solution of dimethylamine (100 ml) added dropwise at 0°–5° with vigorous stirring. The mixture was stirred for 1 hour then ethanol (100 ml) added and the resulting single phase solution was allowed to stand at room temperature for 18 hours. Evaporation of the organic solvent gave an aqueous solution which was adjusted to pH 5 and extracted with dichloromethane (2×100 ml) then the pH raised to µ9.5-10 and extracted with dichloromethane (6×100 ml) at this pH. These latter extracts were dried and evaporated to a mixture of oil and solid. This was taken up in petroleum spirit (100 ml), the insoluble material filtered off and the solution evaporated to give 3-dimethylamino-N,N-dimethylpropanamide as a light brown oil (16.46 g, 76% yield).

(b) A suspension of 1% cross-linked chloromethyl-substituted polystyrene beads (4.0 g, 3.72 meq Cl/g) in dimethylformamide (DMF) (40 ml) was treated with 3-dimethylamino-N,N-dimethylpropanamide (6.5 g) at 65° for 24 hours. The polymer was filtered off and washed with DMF, methanol and diethyl ether and dried in vacuo to give N,N-dimethyl-N-(2-(N,N-dimethylcarbamoyl)ethyl)-ammoniomethyl-substituted polystyrene, chloride salt, as white polymer beads (5.20 g, 2.34 meq Cl−/g).

EXAMPLE 2

(a) 3-Bromopropionyl chloride (25.7 g) was dissolved in dichloromethane (150 ml), cooled to −10° and a solution of octylamine (20.7 g) in dichloromethane (50 ml) was added over 10 minutes at −10° to 0°. Pyridine (12.7 g) in dichloromethane (50 ml) was added to the white suspension at −10° to 0° giving an orange solution. After stirring for 1 hour at 0°, water (100 ml) was added, the phases separated and the aqueous phase extracted with dichloromethane (2×50 ml). The combined organic extracts were washed with dilute sodium hydroxide and water, dried over MgSO4, filtered through a bed of silica gel and evaporated to give 3-bromo-N-octylpropanamide as a colourless solid (21.49 g, 54%) (mp 48°–55°).

(b) 3-Bromo-N-octylpropanamide (21.3 g) was dissolved in ethanol (50 ml) and a 33% solution of dimethylamine in IMS (100 ml) was added. The solution was allowed to stand at 20° for 72 hours then evaporated to give a yellow oil. This oil was dissolved in dilute HCl to give a solution of pH 4 which was washed twice with dichloromethane, basified with dilute aqueous sodium hydroxide solution and extracted with dichloromethane three times. The latter dichloromethane extracts were dried and evaporated to a pale yellow oil. Distillation of the residue gave 3-dimethylamino-N-octylpropanamide as a colourless oil (15.1 g, 83% yield) (bp 135°–8°/0.15mm).

(c) 1% cross-linked chloromethyl-substituted polystyrene (3.0 g, 4.14 meq Cl/g) was treated with 3-dimethylamino-N-octylpropanamide (8.51 g) in DMF as described in Example 1b to give N,N-dimethyl-N-(2-(N-octylcarbamoyl)ethyl)ammoniomethyl-substituted polystyrene, chloride salt, as white polymer beads (5.33 g, 2.09 meq Cl−/g).

EXAMPLE 3

(a) 5-Bromopentanoyl chloride (15.96 g) [J. Am. Chem. Soc. 49, 1830 (1927)] was dissolved in dichloromethane (100 ml), cooled to 0° and 880 ammonia (20 ml) added over 10 minutes at 0°–10° with vigorous stirring. Water (30 ml) was added, the phases separated and the organic phase washed with dilute HCl and water, dried over potassium carbonate and evaporated to give 5-bromopentanamide as a colourless solid (10.27 g, 71% yield) (mp 75°).

(b) 5-Bromopentanamide (10.11 g) was dissolved in ethanol (50 ml) and a 33% solution of dimethylamine in ethanol (20 ml) added. The solution was allowed to stand at room temperature for 3 hours, more dimethyl amine added (20 ml) and the solution allowed to stand at room temperature for 18 hours. The solution was evaporated to an oil which was dissolved in dilute HCl and the solution of pH 2 was washed twice with dichloromethane, basified with NaOH, saturated with NaCl and extracted 10 times with dichloromethane. The combined latter extracts were dried over K2CO3 and evaporated to give 5-dimethylaminopentanamide as acolourless solid (5.72 g, 70%) (mp 86°–7°).

(c) The above amine (4.03 g) was reacted with 1% cross-linked chloromethyl-substituted polystyrene (2.5 g, 3.72 meq/g) by the method described in Example 1b to give N,N-dimethyl-N-(4-carbamoylbutyl)ammoniomethyl-substituted polystyrene, chloride salt, as white polymer beads (3.7 g, 2.56 meq Cl−/g).

EXAMPLE 4

(a) 5-Bromopentanoyl chloride (18.5 g) was dissolved in dichloromethane (100 ml), cooled to 0° and a 25% solution of dimethylamine in water (100 ml) added dropwise at 0°–5° with vigorous stirring. The mixture was stirred for 3 hours then ethanol (100 ml) added and the solution allowed to stand at room temperature for 3 days. After evaporating the organic solvents, the solution was acidified with HCl and washed with dichloromethane then basified with sodium hydroxide, extracted with dichloromethane and the latter organic extracts dried over K2CO3 and evaporated to give 5-dimethylamino-N,N-dimethylpentanamide as a light brown oil (14.48 g, 90%).

(b) The above amine (7.69 g) was reacted with 1% cross-linked chloromethyl-substituted polystyrene (4.0 g, 3.72 meq/g) by the method described in Example 1b to give N,N-dimethyl-N-(4-(N,N-dimethylcarbamoyl)-butyl)ammoniomethyl-substituted polystyrene, chloride salt, as polymer beads (6.4 g, 2.37 meq Cl−/g).

EXAMPLE 5

(a) 5-Bromo-N-octylpentanamide (17.49 g) (mp µ30°) was prepared from 5-bromopentanoyl chloride (12.96 g) and octylamine (9.05 g) by an analogous method to that described in Example 2a.

(b) 5-Bromo-N-octylpentanamide (17.25 g) was dissolved in ethanol (50 ml) and a 33% solution of dimethylamine in ethanol (20 ml) was added. The solution was allowed to stand at room temperature for 3 hours, more dimethylamine (10 ml) added and the solution allowed to stand at room temperature for 18 hours. The solution was evaporated to give an oil, which was dissolved in dilute HCl and the solution at pH 5.5 was washed with dichloromethane. The pH was then raised to 7.5 and extracted twice with dichloromethane at this pH. The combined latter organic extracts were dried over $MgSO_4$ and evaporated to give 5-dimethylamino-N-octylpentanamide as an oil (10.6 g, 70%).

(c) A suspension of 1% cross-linked chloromethyl-substituted polystyrene (3.0 g, 3.72 meq Cl/g) in DMF was treated with 5-dimethylamino-N-octylpentanamide (8.58 g) to give, after work up as described in Example 1b, N,N-dimethyl-N-(4-(N-octylcarbamoyl)butyl)ammoniomethyl-substituted polystyrene, chloride salt, as polymer beads (5.96 g, 1.97 meq $Cl^-$/g).

EXAMPLE 6

1% cross-linked chloromethyl-substituted polystyrene (10 g, 3.72 meq Cl/g) was treated with dimethylamine (200 ml of 33% solution in ethanol) in DMF (100 ml) to give N,N-dimethylaminomethyl-substituted polystyrene (10.41 g, 3.52 meq N/g). A suspension of this amino-substituted polystyrene (2.84 g) in DMF (50 ml) was treated with methyl 8-bromooctanoate (11.85 g) and the mixture heated at 60° for 48 hours. The polymer was filtered off and washed with ethanol and diethyl ether and dried in vacuo to give N-(7-methoxycarbonylheptyl)-N,N-dimethylammoniomethylated polystyrene, bromide salt, as white polymer beads (4.74 g, 2.04 meq $Br^-$/g, 2.03 meq N/g).

EXAMPLE 7

(a) A solution of 4-cyclohexanebutyric acid (11.0 g) in dry tetrahydrofuran (150 ml) was treated sequentially with triethylamine (8.14 g), ethyl chloroformate (8.75 g) and N,N-dimethylethylenediamine (8.51 g) to give, after work-up, N-(2-(4-cyclohexanebutyramido)ethyl)-N,N-dimethylamine as a colourless oil (14.71 g).

(b) A suspension of 1% cross-linked chloromethyl-substituted polystyrene (2.0 g, 3.72 meq Cl/g) in DMF (50 ml) was treated with the above amine (2.7 g) at 70° for 24 hours. A further quantity of the amine (1.0 g) in DMF (20 ml) was added and the mixture stirred at 70° for 3 hours, methanol (20 ml) added and stirred for 1 hour. The polymer was filtered off and washed with DMF, methanol, water, methanol and diethyl ether and dried to give N-(2-(4-cyclohexanebutyramido)ethyl)-N,N-dimethylammoniomethyl-substituted polystyrene, chloride salt, as white polymer beads (3.60 g, 2.05 meq $Cl^-$/g).

EXAMPLE 8

(a) A mixture of 3-(N,N-dimethylamino)propylamine (51.1 g) and anhydrous sodium carbonate (1.06 g) in diethyl ether (500 ml) was cooled in ice bath. To this mixture trifluoroacetic anhydride (84.8 ml) was added dropwise. The mixture was stirred at room temperature overnight, then diluted with water and extracted with diethyl ether. The ether extract was washed with saturated aqueous sodium chloride solution, dried and evaporated to give 3-(N,N-dimethylamino)propyl-N-trifluoroacetamide (52.87 g, 53.5%).

(b) 1% cross-linked chloromethyl-substituted polystyrene beads (5.0 g, 3.72 meq Cl/g) were suspended in DMF (50 ml) and 3-(N,N-dimethylamino)propyl-N-trifluoroacetamide (18.5 g) added. The mixture was stirred at 60° for 18 hours. The polymer was filtered off, washed with methanol and diethyl ether and dried at 90°/0.5mmHg for 18 hours to give N,N-dimethyl-N-(trifluoroacetamidoprop-3-yl)-ammoniomethyl-substituted polystyrene, chloride salt, as white beads (9.36 g, 2.10 meq $Cl^-$/g, 4.10 meq N/g).

EXAMPLE 9

A suspension of 1% cross-linked chloromethyl-substituted polystyrene (20 g, 4.22 meq Cl/g) in DMF (200 ml) was treated with 3-dimethylaminopropan-1-ol (13.05 g) at 70° for 7 hours. The polymer was filtered off and washed with DMF, methanol, water, and diethyl ether and dried in vacuo to give N-(3-hydroxypropyl)-N,N-dimethylammoniomethyl-substituted polystyrene, chloride salt, as white polymer beads (28.9 g, 2.56 meq $Cl^-$/g).

EXAMPLE 10

A suspension of 1% cross-linked chloromethyl-substituted polystyrene (4.08 g, 3.72 meq Cl/g) in DMF (40 ml) was treated with 11-(N,N-dimethylamino)-undecan-1-ol (5.49 g) at 60° for 12 hours. The polymer was filtered off and washed with DMF, methanol, and diethyl ether and dried in vacuo for 12 hours to give N,N-dimethyl-N-(11-hydroxyundecyl)ammoniomethyl-substituted polystyrene, chloride salt, as white polymer beads (7.3 g, 2.14 meq $Cl^-$/g).

EXAMPLE 11

A solution of N,N-dimethyl-N-(11-hydroxyundecyl) amine (1.1 g), triphenylphosphine (1.34 g) and phthalimide (0.75 g) in dry THF (20 ml) was treated with diethylazodicarboxylate (0.94 g, 95%). The resultant mixture was stirred for 18 hours, evaporated to dryness and the residue triturated with ether. The precipitated crystals were removed by filtration. The filtrate was evaporated to dryness and the residue was chromatographed on silica gel, eluted with chloroform and then chloroform:methanol:methanolic ammonia (89:10:1), to give N,N-dimethyl-N-(11-phthimidoundecyl)amine (0.75 g) as a brown, low melting solid.

This amine (13.01 g) was mixed with chloromethylated polystyrene (5.1 g, 3.72 meq Cl/g) in DMF (50 ml) and stirred at 60° for 12 hours. After work up as described in Example 1, N,N-dimethyl-N-(11-phthamidoundecyl)-ammoniomethyl-substituted polystyrene, chloride salt was obtained as a cream coloured resin (11.70 g).

EXAMPLE 12

N,N-Dimethyl N-(11-phthalimidoundecyl)amine (22.9 g) (Example 11) was added to hydrazine hydrate (3.54 g) in ethanol (200 ml), and refluxed for 7 hours. The solvent was removed leaving a white solid, which was partially dissolved in dilute hydrochloric acid and filtered. The pH of the filtrate was adjusted to pH 14 using NaOH (1M) whereupon a brown oil separated from the aqueous phase and was extracted with ether. The organic extract was dried and evaporated to give N,N-dimethyl-N-(11-aminoundecyl)-amine as a brown oil (9.5 g).

A solution of this amine (4.6 g) in dilute hydrochloric acid (40 ml) and concentrated hydrochloric acid (12 ml) was treated with potassium cyanate (7.0 g) in water (10 ml). The mixture was refluxed for 18 hours and the solvent removed leaving a white solid. To this methanol (10 ml) was added and the mixture filtered. The solvent was evaporated from the filtrate which was then chromatographed on a basic alumina column eluting with 10% methanol in chloroform, to give a yellow solid which was washed with ether to give N,N-dimethyl-N-(11-ureidoundecyl)amine as a white solid (1.2g).

This amine (1.01 g) was mixed with chloromethylated styrene (0.95 g, 3.72 meq Cl/g) in DMF (12 ml) and stirred at 60° for 20 hours. The polymer was filtered, washed with DMF, methanol and ether prior to drying at 80°, 0.5 mmHg for 24h to give N,N-dimethyl-N-(11-ureidoundecyl)-ammoniomethyl-substituted polystyrene, chloride salt, as a white solid (1.82 g, 1.92 meq Cl-/g).

What is claimed is:

1. A polymer of structure (I)

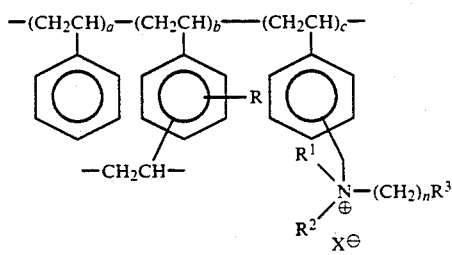

in which,

R is hydrogen or $R^1R^2{}^{\oplus}N(CH_2)_nR^3$;

$R^1$ and $R^2$ are each $C_{1-4}$ alkyl;

$R^3$ is $CONR^4R^5$, $NR^4COR^6$, a phthalamido group or $COR^7$;

$R^4$ and $R^5$ are the same or different and are each hydrogen or $C_{1-8}$alkyl;

$R^6$ is $C_{1-4}$alkyl, $C_{1-4}$alkyl$C_{3-6}$cycloalkyl, $CF_3$ or $NR^4R^5$;

$R^7$ is hydroxy, $C_{1-4}$alkyl or $C_{1-4}$alkoxy; n is 2 to 12;

a, b and c are numbers which indicate the relative molar percentages of the units present in said polymer, (b) being from 1 to 10 molar percent, and (c) being from 30 to 98 molar percent;

$X^{\ominus}$ is a counter ion; except compounds in which n is z and $R^3$ is OH.

2. A polymer according to claim 1 in which $R^1$ and $R^2$ are each methyl.

3. A polymer according to claim 2 in which (b) is from 2 to 8 molar percent of said polymer.

4. A pharmaceutical composition comprising a polymer of structure (I) as claimed in claim 1 in association with a pharmaceutically acceptable carrier.

5. A polymer according to claim 1 that is a N,N-dimethyl-N-(11-ureidoundecyl)-ammoniomethyl-substituted polystyrene derivative.

6. A polymer according to claim 1 that is a N,N-diemthyl-N-(4-(N-octylcarbamoyl)butyl)ammoniomethyl-substituted polystyrene derivative.

7. A polymer according to claim 1 that is a N-(7-methoxycarbonylheptyl)-N,N-dimethylammoniomethylated polystyrene derivative.

8. A polymer according to claim 1 that is a N-(2-(4-cyclohexanebutyramido)ethyl)-N,N-dimethylammoniomethyl-substituted polystyrene derivative.

9. A polymer according to claim 1 that is a N,N-dimethyl-N-(2-(N-octylcarbamoyl)ethyl)ammoniomethyl-substituted polystyrene derivative.

10. A polymer according to claim 1 that is a N,N-dimethyl-N-(trifluoroacetamidoprop-3-yl)-ammoniomethyl-substituted polystyrene derivative.

11. A pharmaceutical composition according to claim 4 wherein the polymer is a N,N-dimethyl-N-(11-ureidoundecyl)-ammoniomethyl-substituted polystyrene derivative.

12. A pharmaceutical composition according to claim 4 wherein the polymer is a N,N-diemthyl-N-(4-(N-octylcarbamoyl)butyl)ammoniomethyl-substituted polystyrene derivative.

13. A pharmaceutical composition according to claim 4 wherein the polymer is a N-(7-methoxycarbonylheptyl)-N,N-dimethylammoniomethylated polystyrene derivative.

14. A pharmaceutical composition according to claim 4 wherein the polymer is a N-(2-(4-cyclohexanebutyramido)ethyl)-N,N-dimethylammoniomethyl-substituted polystyrene derivative.

15. A pharmaceutical composition according to claim 4 wherein the polymer is a N,N-dimethyl-N-(2-(N-octylcarbamoyl)ethyl)ammoniomethyl-substituted polystyrene derivative.

16. A pharmaceutical composition according to claim 4 wherein the polymer is a N,N-dimethyl-N-(trifluoroacetamidoprop-3-yl)-ammoniomethyl-substituted polystyrene derivative.

* * * * *